(12) United States Patent
Sato et al.

(10) Patent No.: US 10,137,569 B2
(45) Date of Patent: Nov. 27, 2018

(54) MULTI-ARTICULATED MANIPULATOR

(71) Applicant: NIPPON THOMPSON CO., LTD., Tokyo (JP)

(72) Inventors: Takashi Sato, Mino (JP); Tetsuya Sakai, Mino (JP)

(73) Assignee: NIPPON THOMPSON CO., LTD., Tokyo (JP)

( * ) Notice: Subject to any disclaimer, the term of this patent is extended or adjusted under 35 U.S.C. 154(b) by 156 days.

(21) Appl. No.: 15/175,420

(22) Filed: Jun. 7, 2016

(65) Prior Publication Data
US 2017/0050313 A1   Feb. 23, 2017

(30) Foreign Application Priority Data
Aug. 19, 2015   (JP) .................................. 2015-162108

(51) Int. Cl.
*B25J 17/00* (2006.01)
*B25J 17/02* (2006.01)
*B25J 18/00* (2006.01)
*B25J 9/06* (2006.01)
*B25J 15/00* (2006.01)

(52) U.S. Cl.
CPC ............. *B25J 9/06* (2013.01); *B25J 15/0028* (2013.01); *B25J 18/002* (2013.01)

(58) Field of Classification Search
CPC ............ B25J 15/0028; A61B 2034/305; A61B 17/22031; A61B 2017/2908; A61B 2017/2938
See application file for complete search history.

(56) References Cited

U.S. PATENT DOCUMENTS 5,817,119 A  * 10/1998  Klieman ................ A61B 17/29
                                                        606/170
2014/0379014 A1 * 12/2014  Abri ................... A61B 17/2804
                                                        606/170

FOREIGN PATENT DOCUMENTS

JP     2005169011 A     6/2005
JP     2007292276 A    11/2007

* cited by examiner

*Primary Examiner* — Jake Cook
(74) *Attorney, Agent, or Firm* — Browdy and Neimark, PLLC

(57) ABSTRACT

A multi-articulated manipulator is operated without rickety movement by a pair of grasping members, springs for the grasping members, and other springs extended across the foremost outer shell and the basement outer shell. The manipulator is small in size, easy to handle, reliable, better response and high precision in medical applications. With the multi-articulated manipulator, the foremost outer shell is connected to the basement outer shell in a bending manner. A pair of grasping members of claw members is connected to the foremost end of the foremost outer shell. The claw members are operated with a pair of claw power-transmission shafts and energized with springs to be biased towards their closed situation. The foremost outer shell and the basement outer shell are operated with claw power-transmitting shaft and normally biased by springs towards their closed situation.

9 Claims, 7 Drawing Sheets

MULTI-ARTICULATED MANIPULATOR

FIELD OF THE INVENTION

The present invention relates to a manipulator or a forceps having more than one articulation, which is adapted for a variety of instruments applied to for example medical robots, medical instruments, manipulators and the like.

BACKGROUND OF THE INVENTION

A conventional driving mechanism for surgical manipulator is disclosed in, for example, Published Unexamined Patent Application in Japan No. 2007-292 276, which is energized with an input of rotation to make a bending and/or curvature movement on connecting members. With the driving mechanism as cited earlier, the manipulator has a bending link to join adjacent connecting members each other and grasping links. The grasping links are connected to the connecting members against axial direction. The grasping links each have a first shaft and a second shaft, the first shaft having second male threads mating with a second plate of the connecting member and the second shaft having first male threads mating with a first plate of the connecting member. The first and second male threads are made inversely each other with the same pitch. With the relation of the male threads around the shafts, the connecting members moves to approach each other when the bending link is rotated in any one direction, whereas the connecting members moves away from each other when the bending link is rotated in opposite direction.

Moreover, a multi-freedom manipulator is disclosed in, for example, Published Unexamined Patent Application in Japan No. 2005-169 011, which is superior durability and accuracy in control, and further easier in attaching and/or detachability to the sterilizers, washers and driving means. The multi-freedom manipulator has at least three freedom of relative opening/closing movement of a pair of grasping members, rotation of grasping members around a first axis, and rotation of the grasping members around a second axis lying on an imaginary plane perpendicular to the first axis. With the multi-freedom manipulator constructed as stated earlier, the power applied from the actuator is converted through first ~three link mechanisms into relative opening/closing movement of the grasping members, rotating movement around a first axis and rotating movement around a second axis.

With the prior wire-operated medical manipulator, moreover, the working parts on the foremost ends of the medical forceps are mainly actuated with a wire for power transmission. Because of this, any lag may occur in tensile variation of expansion and/or contraction of the wire. There causes a problem of worse response or follow-up property which would interfere any minute movement. With the prior wire-operated medical manipulator, moreover, there occur any obstacles or troubles of wire-breakage, elongation and so on which would obstacle accurate operation and/or certain power-transmission. With the patent literature recited earlier, the driving mechanism is disclosed in which rotation of the connecting parts is input to actuate the forceps to bend or curve the connecting parts. The limiting universal joints and the driving universal joints are combined to be actuated to get the whole driving part bending. Thus, when the driving mechanism constructed as stated is made small in construction, the housing therefor has to be constituted with three universal joints, with the problems of becoming large in warp and less in rigidity. As a result, the joints can't be bent independently from each other and, therefore, are difficult to make fine movements. The multi-freedom manipulator, because constructed in such that the linkage is driven by fore-and-aft movement transmitted from the actuator and joints are constituted to make bi-axial movement of vertical and sidewise directions, has problems that it is unfit to make fine movement at every joint and the linkage is slender and so long as to lessen in rigidity.

In co-pending Patent Application in Japan No. 2015-34 905, there is disclosed a multi-freedom manipulator which is rich in reliability and follow-up property and operable with high accuracy when used in medical instruments. The multi-freedom manipulator is composed of more than one hollow outer shell, a joint to connect the adjacent outer shells each other in a rocking manner, grasping members mounted to the foremost outer shell to be actuated to hold any object between them, a claw power-transmitting shaft to actuate claws of the grasping members in a rocking manner, and an outer shell power-transmitting shaft to actuate the outer shell in a bending manner. The claw power-transmitting shaft and the outer shell power-transmitting shaft are each composed of a foldable universal joint to transmit a torque, and an expandable power-transmitting shaft to transmit a torque. The power-transmitting shaft has male threads mated with a nut made in a boss portion inside the outer shell.

SUMMARY OF THE INVENTION

The present invention has for its primary object to resolve the major problems as stated earlier, and to provide a manipulator of multi-articulated construction particularly suitable for medical instruments, which has joints at two locations to simplify the construction. More particularly, two outer shells are connected lengthwise in series in folding manner The foremost outer shell has a pair of grasping members including claw members to grasp any object between them. One of the opposed outer shells is actuated with the outer shell power-transmitting shaft in a bending manner to operate a pair of claw members independently from each other in opposite directions or the same direction. Especially, a pair of claw members has a first spring respectively to protect any wobbling between the claw members. A second spring is provided between the basement outer shell and the foremost outer shell to prevent any rickety movement. Moreover, the basement outer shell has an outer shell power-transmission shaft and two lines of claw power transmission shafts, and the foremost outer shell has therein two claw power-transmission shafts. The construction as stated just earlier helps to reduce the numbers of the joints and the power-transmission shafts and further helps making the basement outer shell and the foremost outer shell to reduce in their diameters as less as possible. The outer shell and the power-transmission shafts are made of metallic material to make certain of enough rigidity with less tensile changes owing to expansion of the power-transmission shaft. The power-transmission shaft is allowed to operate in a simple manner and make better the response or follow-up property of the operation of the outer shell and the claw members, thereby making it possible to operate the claw members with highly accurate, fine and proper closing/opening operation.

Subject to be Solved with the Present Invention

The present invention relates to a multi-articulated manipulator more than one hollow outer shells, grasping members at a foremost end of the outer shell, and more than one power-transmission shaft to actuate the outer shell and the grasping members, wherein the outer shells are composed of a foremost outer shell connecting the grasping members to the foremost end of the outer shell and a basement outer shell connected to the foremost shell for bending manner, wherein the power-transmission shaft is inserted in the basement shell and foremost outer shell, and provided with a pair of claw power-transmission shafts operated independently from each other to actuate a pair of claw members of the grasping members, and wherein the claw members are operated independently from each other by respective independent operation of each of the claw power-transmission shafts around a first fulcrum of a first fulcrum pin fastened in a diametrical direction of the foremost end of the foremost outer shell, and a first spring is installed respectively to the claw member in such a manner extending around the first fulcrum to energize a tensile force to urge the claw members towards a closed situation.

In the present invention, there is disclosed a multi-articulated manipulator composed of a first articulation connecting in operative manner claw members of grasping members to the foremost end of a foremost outer shell, and a second articulation connecting the foremost outer shell to a basement outer shell in a bending manner.

In the present invention, there is disclosed a multi-articulated manipulator in which a base portion of the claw member is formed in a cylindrical boss portion having the first fulcrum at the center thereof, and the claw members are normally energized with a spring force which acts to pull towards each other between a first fixed pin held at an end thereof to lie on a cylindrical surface of the boss portion and a second fixed pin held at another end thereof inside the foremost outer shell.

In the present invention, there is disclosed a multi-articulated manipulator in which the foremost outer shell is connected to the basement outer shell so as to make a bending movement in the single direction around a second fulcrum of a second fulcrum pin fastened in a radial direction of respective joints between the foremost outer shell and the basement outer shell. In a further another aspect of the present invention, there is disclosed a multi-articulated manipulator in which a second spring is mounted across the foremost outer shell and the basement outer shell to keep the foremost outer shell in a straight condition with respect to the basement outer shell, and the second spring extends between a third pin fastened to the foremost outer shell and a fourth pin fastened, with passing through a location biased from the second fulcrum to thereby energize normally a spring force acting in a direction to pull mutually the foremost outer shell and the basement point each other. With the multi-articulated manipulator stated here, cut-away portions to relieve the second spring are provided in a lengthwise direction to extend in axial direction at opposed ends of the foremost outer shell and the basement outer shell located biased towards the spring.

In the present invention, there is disclosed a multi-articulated manipulator in which the claw power-transmission shaft has a universal joint at a location corresponding to a joint between the foremost outer shell and the basement outer shell, and a first linkage mechanism to operate the claw members connected with the foremost outer shell around the first fulcrum point in response to the bending movement between the foremost outer shell and the basement outer shell, and further in which the first linkage mechanism includes a first nut having first male threads mating with first female threads made on male threads formed on a foremost end of the claw power-transmission shaft, and a first linkage member to connect the first nut with the claw member whereby while rotation of the claw power-transmission shaft, the first nut moves in axial direction along the first male threads and the first linkage moves in an axial direction along the first male threads, whereby the first linkage member actuates the claw members around the first fulcrum. Moreover, the foremost end of the foremost outer shell has a lengthwise slit to escape the first linkage members to protect the first linkage member against interference with rotation of the linkage member.

In the present invention, there is disclosed a multi-articulated manipulator in which the outer shell power-transmitting shaft to actuate the foremost outer shell relatively to the basement outer shell has a second linkage mechanism inserted into the basement outer shell to bend the foremost outer shell, and wherein the second linkage mechanism is composed of a second male threads formed at the foremost end of the outer shell power-transmission shaft, a second nut having a second female threads mating with the second male threads, and a second linkage member to connect the second nut with the foremost outer shell, and further wherein the second nut moves in an axial direction along the second male threads upon rotation of the outer shell power-transmitting shaft and the foremost outer shell makes bending movement in the single direction around the second fulcrum point relatively to the basement outer shell.

Effect of the Invention

The multi-articulated manipulator of the present invention is composed of only the foremost outer shell and the basement outer shell arranged in an axial direction, the grasping members connected to the foremost outer shell, and three power-transmission shafts inserted in the in the basement outer shell. Thus, the foremost outer shell and the basement outer shell are allowed to have outer diameters as small as possible. Moreover, since there are provided the first spring to urge the claw members to close each other, there is no fear of getting rickety in operation of the claw members. In addition, there is no fear in getting rickety in bending operation between the foremost outer shell and the basement outer shell. With the multi-articulated forceps having two articulations of the present invention, springs installed at every articulation protect the forceps against rickety movement. Thus, the forceps become easier in manipulation thereof to make sure of certain operation. Moreover, with the multi-articulated manipulator of the present invention, the paired claw members, even if opened for example to the maximum limit, are protected from falling into the condition of remained impossible to be operated because of the spring force exerting to close the forceps. With the multi-articulated forceps constructed as stated earlier, the paired claw members of the grasping members may be operated independently from each other by means of the paired claw power-transmission shaft. The foremost outer shell may be moved quickly and easily with better follow-up property relatively to the basement outer shell by means of the outer shell power-transmission shaft in a single direction, for example in a vertical direction or sidewise direction towards an appropriate predetermined location. As the male threads on the foremost end of each power-transmitting shaft mate with the nut on the outer shell, only the rotation of the power-transmitting shaft pulls or draws the link members of the linkage mechanism to get the foremost outer shell bending immediately across a wide angular range. In addition, the multi-articulated forceps of the present invention is easy in operation and rich in reliability and further better in follow-up property of the operations of the outer shell and the grasping members so as to display the appropriate operations with accuracy. Thus, the present invention preferably realizes better operation of the multi-articulated forceps for medical use.

DETAILED DESCRIPTION OF THE EMBODIMENT

Figure 1:
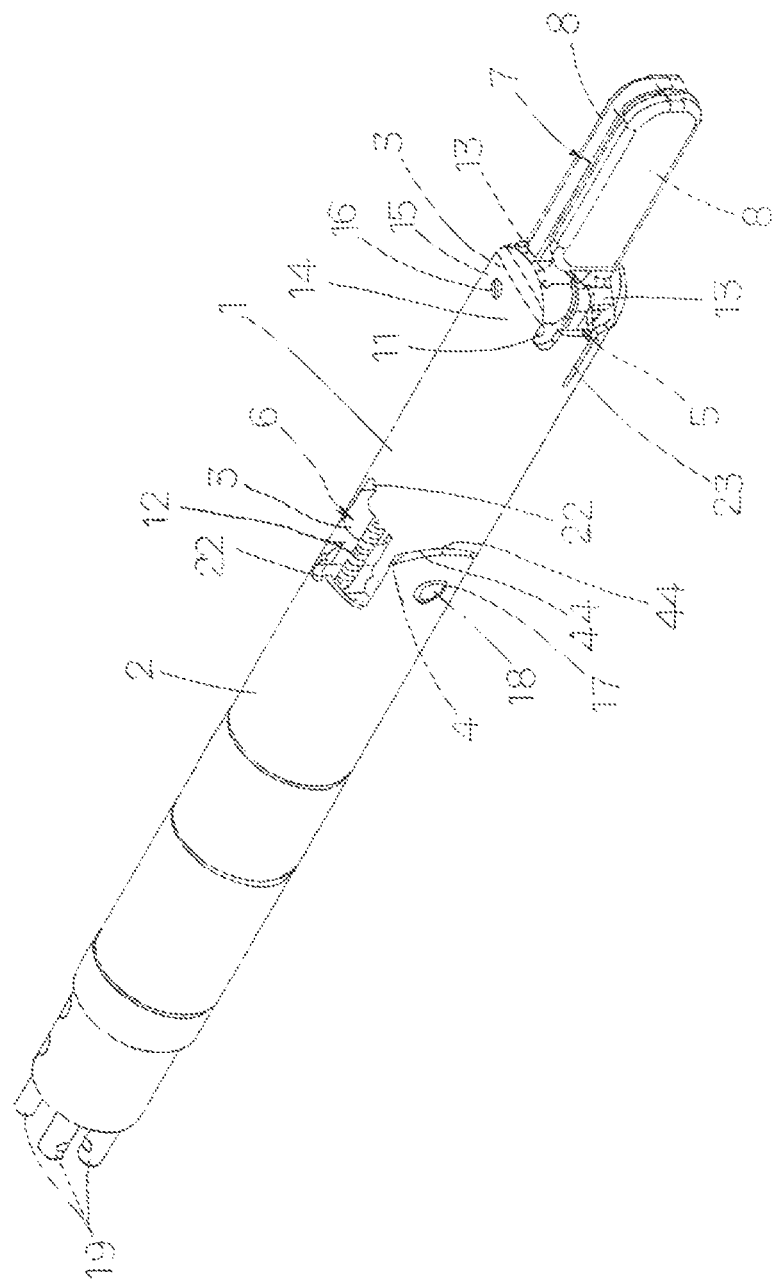
FIG. 1 is a perspective view showing a preferred embodiment of a multi-articulated forceps according to the present invention.

The manipulator or forceps having more than one articulation of the present invention is adapted for a variety of instruments applied to for example medical robots, medical instruments, and the like.

The manipulator or forceps having more than one articulation of the present invention will be explained in detail with reference to the accompanying drawings. In general, the manipulator or forceps having more than one articulation of the present invention has more than one hollow outer shells or a foremost outer shell 1 and a basement outer shell 2 connected to the foremost outer shell 1 for bending movement, grasping members 7 connected to a foremost end 14 of the foremost outer shell 1, an outer shell power-transmission shaft 10 to actuate the foremost outer shell 1 in a bending manner with respect to the basement outer shell 2, and two lines of claw power-transmission shafts 9 to actuate claw members 8 of the grasping members 7 relatively to each other. The grasping members 7 have a pair of the claw members 8 jointed to the foremost end 14 of the foremost outer shell 1. The paired claw members 8 are actuated through the claw power-transmission shafts 9 to grasp or hold any object between them. With the multi-articulated manipulator as stated earlier, the foremost outer shell 1 and the basement outer shell 2 are connected each other at a joint 4 for bending movement through an articulation 6 (second articulation). Moreover, a joint 3 lying between the foremost outer shell 1 and the grasping members 7 provides an articulation 5 (first articulation) to operate the claw members 8. With the multi-articulated manipulator constructed as stated earlier, there are made the articulation 5 in which the claw members 8 of the grasping members 7 are connected each other to make closing/opening movement at the joint 3, and the articulation 6 in which the foremost outer shell 1 and the basement outer shell 2 are connected each other at the joint 4 for bending movement. Thus, multi-articulated manipulator constructed as stated earlier as a whole is simplified and small-sized in construction. More especially, the power-transmission shafts 9, 10 have a pair of claw power-transmission shafts 9 and outer shell power-transmission shafts 10. The claw power-transmission shafts 9 extend through the foremost outer shell 1 and the basement outer shell 2 to actuate the paired claw members 8 for the grasping members 7 independently from each other. The outer shell power-transmission shafts 10 extend through the basement outer shell 2 to operate the paired claw members 8 independently from each other to bend the foremost outer shell 1 in one direction with respect to the basement outer shell 2. With the multi-articulated manipulator of the present invention, the outer shells 1, 2 are made small to have the outer diameter half, as compared with the multi-articulated manipulator disclosed in prior Japanese Patent Application No. 2015-9 257. For example, the outer shells 1, 2 each have an outer diameter of φ 8 mm, the number of the foremost outer shell 1 and the basement outer shell 2 is reduced to three and the articulations are reduced to two locations.

The multi-articulated manipulator of the present invention as described earlier is composed of the foremost outer shell 1 jointed to the foremost end 14, and the basement outer shell 2 jointed to the foremost outer shell 1 for bending manner. With the multi-articulated manipulator constructed as stated earlier, the three lines of the power-transmitting shafts consist of a pair of claw power-transmitting shafts 9 and an outer shell power-transmitting shaft 10. The claw power-transmission shafts 9 extend across both of the basement outer shell 2 and the foremost outer shell 1 to operate in a closing and opening manner the paired claw members 8 independently from each other. The outer shell power-transmitting shaft 10 extends through the basement outer shell 2 to operate the foremost outer shell 1 to bend unidirectionally (for example, in vertical direction). The paired claw members 8 are actuated through independent operation of the respective claw power-transmitting shafts 9 so as to make the closing/opening movement each other around a fulcrum 15 (first fulcrum) composed of a fulcrum pin 16 (first fulcrum pin) fastened in a diametrical direction of the foremost end 14 of the foremost outer shell 1. With the multi-articulated manipulator constructed as stated earlier, an abutment plate 33 is fastened with screws or the like to the foremost outer shell 1. The abutment plate 33 has more than one perforation 47 in which foremost ends of the two claw power-transmitting shafts 9 and the outer shell power-transmitting shaft 10 are fit and born against more than one perforation 47. Each of the paired claw members 8 is operated with independent operation of the respective claw power-transmitting shafts 9 around the fulcrum 15 of the fulcrum pin 16 fastened in the diametrical direction of the foremost end 14 of the foremost outer shell 1. With the multi-articulated manipulator constructed as described earlier, all of the foremost outer shell 1, basement outer shell 2, claw power-transmitting shafts 9 and outer shell power-transmitting shaft 10 are made of metallic material of stainless steel to make sure of any preselected rigidity.

Figure 2:
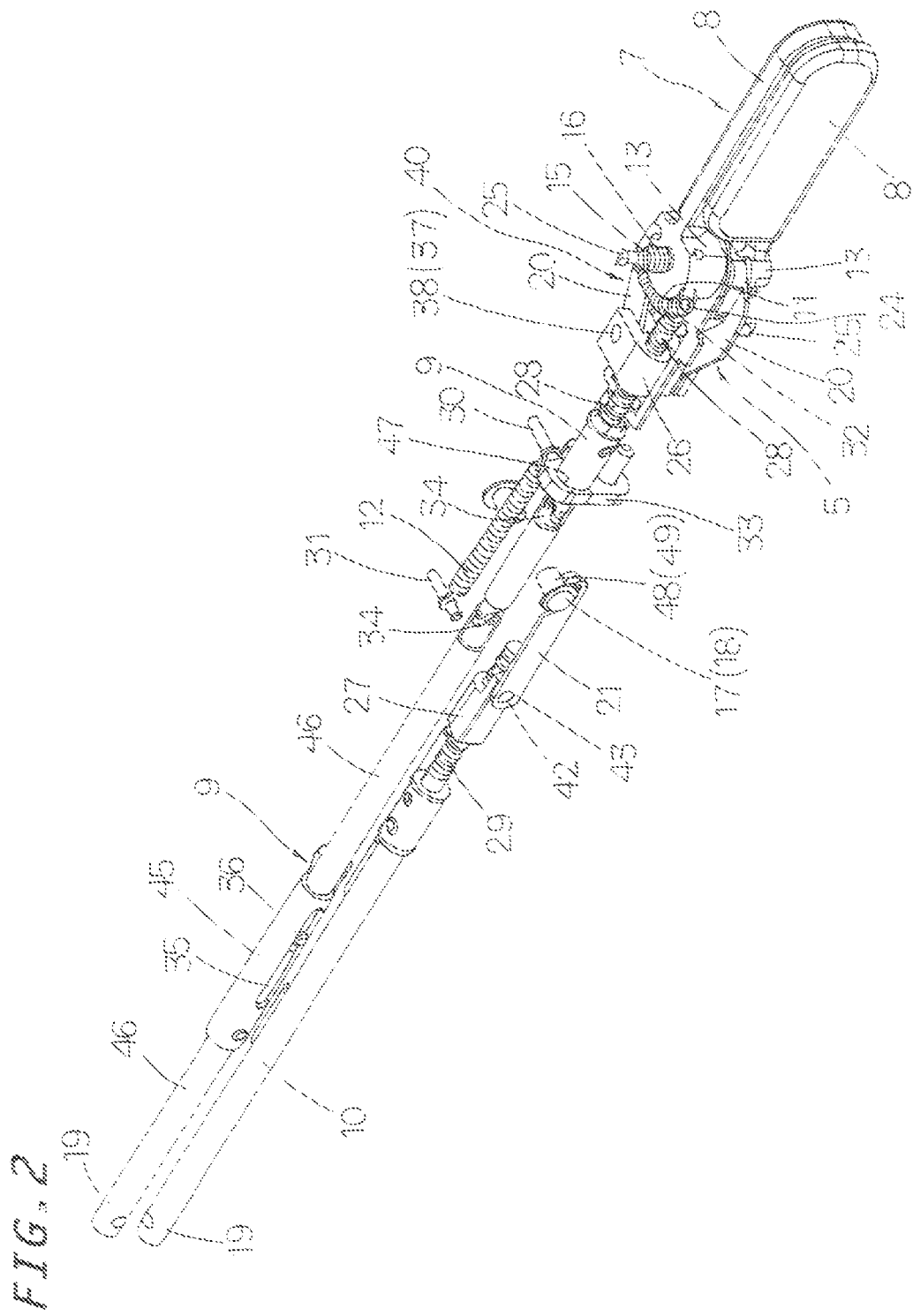
FIG. 2 is a perspective view showing an outer shell power-transmitting shaft and one of a pair of claw-power transmitting shafts, in which a basement outer shell and a foremost outer shell are removed from the multi-articulated forceps of FIG. 1 to show the power-transmitting shaft.
Figure 3:
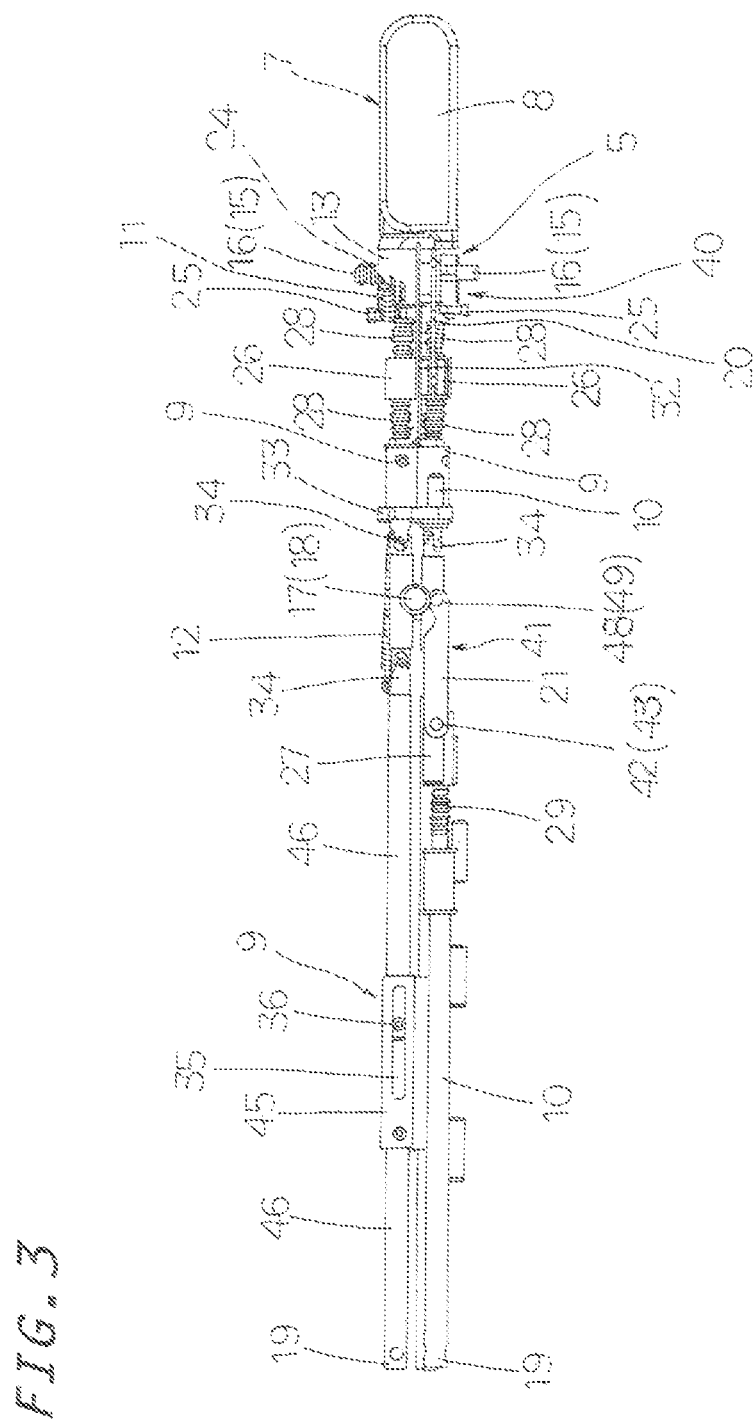
FIG. 3 is a plan view showing the outer shell power-transmitting shaft and the paired claw-power transmitting shafts of FIG. 2.
Figure 4:
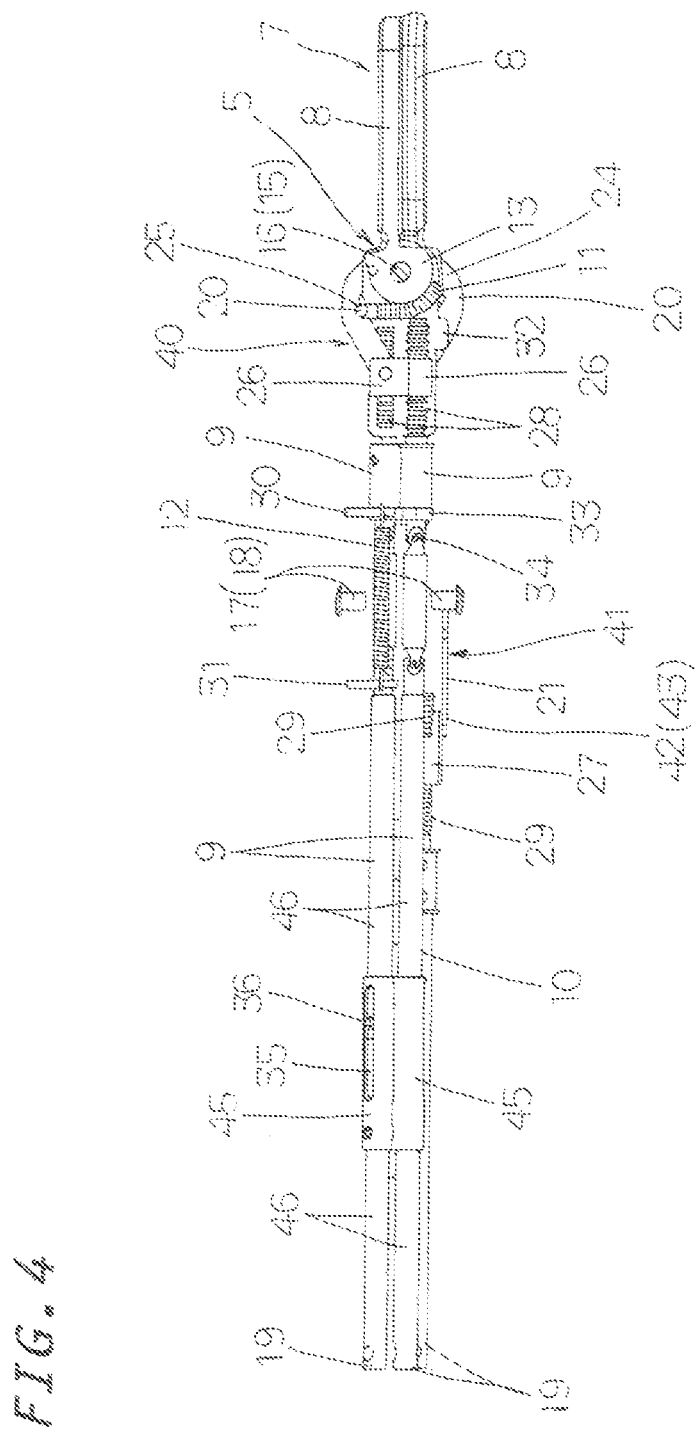
FIG. 4 is a side elevation showing the outer shell power-transmitting shaft and the paired claw-power transmitting shafts of FIG. 3.
Figure 5:
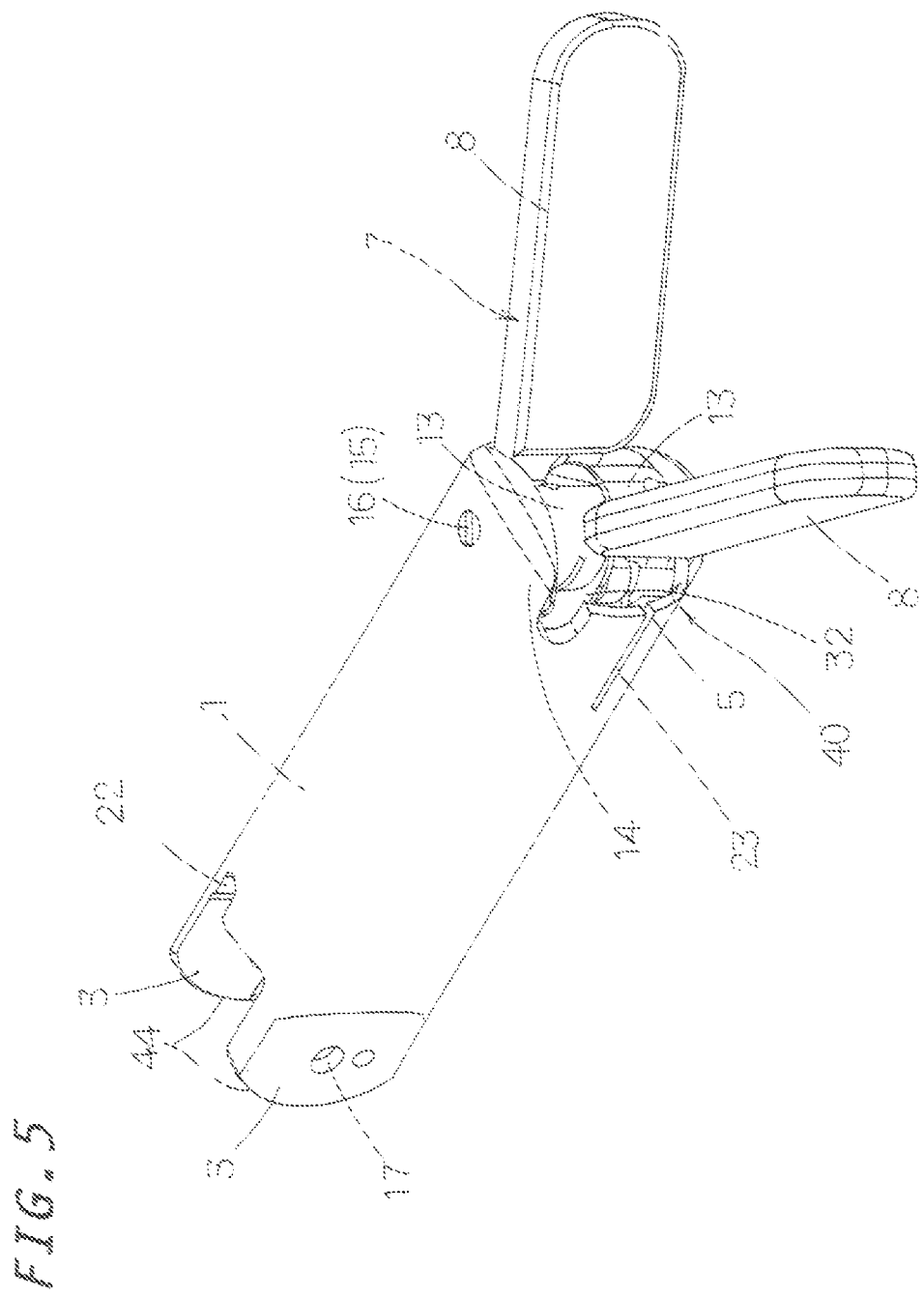
FIG. 5 is a perspective view showing an opened phase of grasping members in the multi-articulated forceps of FIG. 4.
Figure 6:
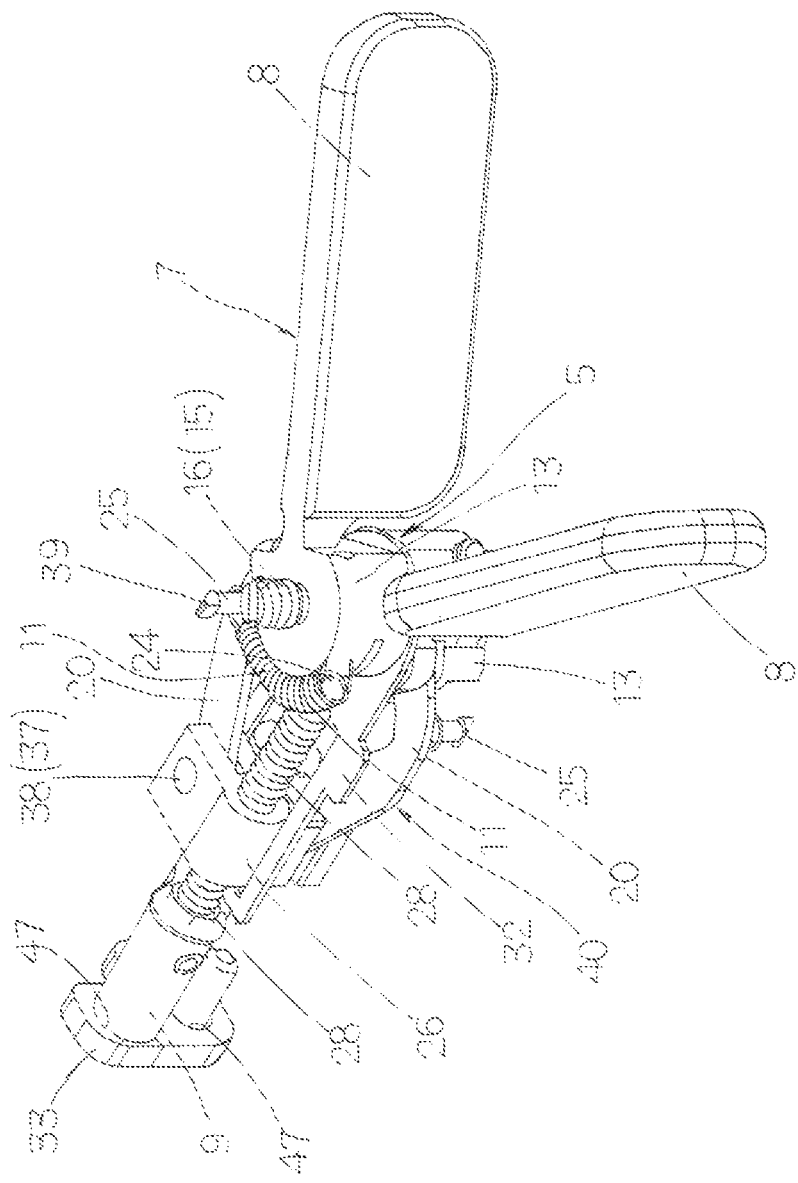
FIG. 6 is a perspective view showing the grasping members, in which the foremost outer shell is removed from the grasping members of FIG. 5.
Figure 7:
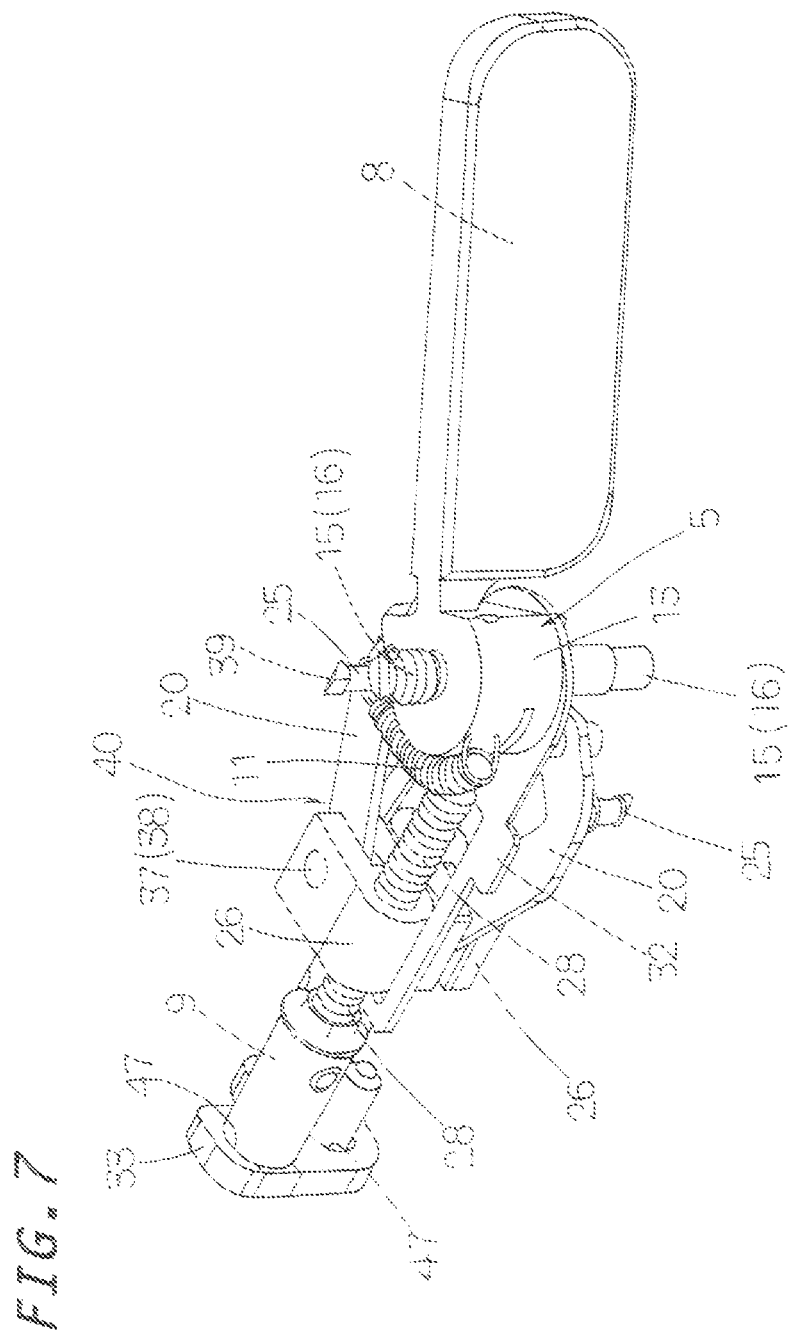
FIG. 7 is a perspective view showing one of the claw members in the grasping members of FIG. 6.

With the multi-articulated manipulator of the present invention, especially as shown in FIGS. 2 to 4, a spring 11 (first spring) is incorporated to reduce any rickety condition which would arise between paired claw members 8 of the grasping members 7 and another spring 12 (second spring) is incorporated to reduce any rickety condition which would arise between the foremost outer shell 1 and the basement outer shell 2. Namely, the claw members 8 have respectively the spring 11 to apply a tensile force to energize the claw members 8 to close each other around the fulcrum 15 of the fulcrum pin 16. With the multi-articulated manipulator of the present invention, moreover, the base of the claw member 8 makes a cylindrical boss portion 13 which has the fulcrum 15 at the center thereof. The spring 11 is made of a coiled spring (first coiled spring). The spring 11 is held at one end thereof to a boss portion 13 to extend between a fixed pin 24 (first fixed pin) lying on a cylindrical surface of the boss portion 13 and another fixed pin 25 (second fixed pin) secured to the foremost outer shell 1. The spring 11 has a tensile force to pull the claw member 8 against each other. Thus, the spring 11 urges the claw members 8 to close each other, thereby functioning to prevent from occurrence of any rickety movement during the movement of the claw members 8.

With the multi-articulated manipulator constructed as stated earlier, the spring 12 to keep the foremost outer shell 1 straight with respect to the basement outer shell 2 is provided across the foremost outer shell 1 and the basement outer shell 2. The spring 12 is provided to extend between a fastened pin 30 (third fixed pin) secured to the foremost outer shell 1 and a fastened pin 31 (fourth fixed pin) secured to the basement outer shell 2. Moreover, the spring 12 lies to extend through a location biased from a fulcrum 17 (second fulcrum) so as to exert a resilient force in which the foremost outer shell 1 and the basement outer shell 2 are pulled towards each other. Moreover, a cut-away portion 22 to relieve the spring 12 is made to extend in axial direction at ends of the foremost outer shell 1 and the basement outer shell 2 located biased to lay the spring 12 therein. With the multi-articulated manipulator constructed as stated earlier, the multi-articulated manipulator constructed as stated earlier, opposing each other are constructed to operate in bending manner through the outer sell power-transmitting shaft 10. More especially, the foremost outer shell 1 and the basement outer shell 2 are connected with each other at the joints 3, 4 by means of the outer shell power-transmission shaft 10 to make the bending movement between the foremost outer shell 1 and the basement outer shell 2 in an unidirectional or same directional movement (up and down directions, left and right directions) around a fulcrum 17 of the fulcrum pin 18 (second fulcrum pin) fastened in the diametrical direction of the respective joints 3, 4 of the foremost outer shell 1 and the basement outer shell 2. Thus, the foremost outer shell 1 is allowed to bend across a wide angle with respect to the basement outer shell 2. Thus, the foremost outer shell 1 and the basement outer shell 2 are connected each other in a bending manner to make a bending movement through the movement of the outer shell power-transmitting shaft in a single direction (for example, vertical direction) around a fulcrum 17 composed of a fulcrum pin 18 fastened in diametrical directions of the joint 3, 4. The joints 3, 4 of the foremost outer shell 1 and the basement outer shell 2 are arranged that the paired joint 3, 4 opposed each other and extended in parallel with each other lie on top of one another. With the embodiment described here, the outer surface of the joint 3 in the foremost outer shell 1 is made concaved to have a haft in thickness and the inner surface of the joint 4 in the basement outer shell 2 is made concaved to have a haft in thickness. The joint 4 is arranged overlapped on the concave in the joint 3 so that the joints 3, 4 are allowed to make the relatively pivotal movement or bending movement with using the fulcrum pin 16 as the fulcrum point 17. The foremost surfaces of the joints 3, 4 are made in arched surfaces. With the embodiment shown here, the joint 3 has an arced surface 44 of a concaved surface and the joint 4 has the arced surface 44 of a convex surface. The arced surfaces 44 are made to keep close sliding-contact between them without causing any clearance between opposed outer surfaces of the joints 3, 4 when the foremost outer shell 1 bends with respect to the basement outer shell 2.

With the multi-articulated manipulator of the present invention, moreover, the paired claw power-transmitting shafts each have a universal joint 34 at a boundary between the foremost outer shell 1 and the basement outer shell 2. The claw power-transmitting shafts each have a linkage mechanism 40 (first linkage mechanism) which is allowed to open/close the claw members 8 connected to the foremost outer shell 1 around the fulcrum 15. The paired claw power-transmission shafts 9 are each composed of a pair of rod members 46 connected each other with a cylindrical member 45 in an expandable manner. The cylindrical member 45 is fastened to one of the rod members 46 and another rod member 46 has a pin 36. The cylindrical member 45 has an axially elongated slot 35. The pin 36 on the rod members 46 fits in a sliding manner into the axially elongated slot 35 on the cylindrical member 45. The claw power-transmission shaft 9 is made in an expandable manner. The linkage mechanism 40 is constituted with a nut 26 (first nut) having female threads mating with male threads 28 (first male threads) made at the foremost end of the claw power-transmission shaft 9, and a linkage member 20 (first linkage member) to connect the nut 26 with the claw member 8. Upon rotating movement of the claw power-transmission shaft 9, while the nut 26 moves linearly along the male threads 28 in an axial direction, the linkage member 20 actuates the claw member 8 to make opening/closing movement around the fulcrum 15.

A spacer plate 32 is interposed between the boss portions 13 of the respective claw members 8 to make sure of respective rotations of the boss portions 13 independently from each other. Moreover, a fixed pin 25 to bear the boss portion 13 for rotation has a foremost head having a slant surface 39 in conformity with an outside peripheral outer surface of the outer shell 1. The fixed pin 25 has no head portion protruding out of the foremost outer shell 1, and the manipulator in size is made within the range of the outside diameter of the foremost outer shell 1 and the basement outer shell 2. Thus, there is no obstacle or projection obstruction around the manipulator. With the multi-articulated manipulator constructed as stated earlier, after the claw power-transmission shaft 9 has been rotated, the male threads 28 made at the foremost end of the claw power-transmission shaft 9 rotates and the nut 26 mating with the male threads 28 moves in the axial direction along the male threads 28. The linear movement of the nut 26 in the axial direction causes the axial movement of the linkage member 20 fastened at one end thereof to the nut 26 together with rocking movement of the linkage member 20 around a fulcrum 37 of a pin 38 made on the nut 26. The linkage member 20 while rocking movement thereof rotates the boss portion 13 around the fulcrum pin 16 to operate the claw members 8 around the fulcrum 15. Moreover, the foremost end 14 of the foremost outer shell 1 has slits 23 which are made at radially opposed locations to extend in an axially direction or lengthwise direction. The slits 23 are to escape the linkage members 20 to protect the linkage members 20 against interference with rotation of the linkage members 20.

With the multi-articulated manipulator constructed as stated earlier, the power-transmitting shaft 10 to actuate the foremost outer shell 1 with respect to the basement outer shell 2 has a linkage mechanism 41 (second linkage mechanism) to bend the foremost outer shell 1 fit into the basement outer shell 2 relatively to the basement outer shell 2. The linkage mechanism 41 is composed of a male threads 29 (second male threads) made at the foremost end of the outer shell power-transmission shaft 10, a nut 27 (second nut) having female threads (second female threads) mating with the male threads 29, and a linkage member 21 (second linkage member) supported at one end thereof with the nut 27 and at another end thereof with the foremost outer shell 1. After manipulator means 19 has rotated the outer shell power-transmission shaft 10, the male threads 29 at the foremost end of the outer shell power-transmission shaft 10 rotates together with the outer shell power-transmission shaft 10 and the nut 27 having the female threads mating with the male threads 29 moves in the axial direction along the male threads 29. The linkage member 21 is fastened at one end thereof to a fulcrum pin 43 or the fulcrum 42 and supported for rotation at another end thereof to a fulcrum pin 49 or the fulcrum 48. As the linkage member 21 moves in a rocking manner around the fulcrum 42 and the linkage member 21 moves in an axial direction along the male threads 29. As a result, the foremost outer shell 1 is bent in only one direction (for example, in vertical direction or sidewise direction) around the fulcrum 17 relatively to the basement outer shell 2. Moreover, with the multi-articulated manipulators disclosed in the embodiment, though the operated direction of the paired claw members 8 and the only one bending direction (for example, vertical direction or sidewise direction) of the foremost outer shell relatively to the basement outer shell 2 are predetermined in perpendicular relation each other, the predetermined directions may be changed or altered in accordance with situations or conditions.

With the multi-articulated manipulator constructed as stated earlier, the foremost outer shell 1 and the basement outer shell 2 may be made to have outside diameters of φ 8 mm. An opening angle of the articulation or joint 5 between the foremost outer shell 1 and the grasping members 7 may be set to 60 degrees in half side or 120 degrees in both sides. The articulation lying between the foremost outer shell 1 and the basement outer shell 2 may be made to have a vertically bending angle of 60 degrees in half side or 120 degrees in both sides. With the multi-articulated manipulator constructed as stated earlier, moreover, as the springs 11, 12 are provided at the articulation or joint 6 between the foremost outer shell 1 and the joints 3, 4 and at the articulation or joint 5 between the foremost outer shell 1 and the grasping members 7, any shaky movement would be restrained which would be caused between the foremost outer shell and the grasping members and/or between the foremost outer shell 1 and the basement outer shell 2. Thus, the operational control would become easier. Moreover, even if after the paired claw members 8 of the grasping member 7 have been opened completely, the claw members 8 easily return to their closed condition by the action of the resilient force of the spring 11 and therefore, there is no fear that the grasping members fall in an uncontrolled manner. With the multi-articulated manipulator disclosed herein, the articulations or joints 5, as being made less to two in locations, is simplified in construction and improved in operating ability.

What is claimed is:

1. A multi-articulated manipulator comprising:
    a plurality of hollow outer shells,
    grasping members comprising a pair of claw members, and
    a plurality of power-transmission shafts to actuate the plurality of outer shells and the grasping members,
    wherein the plurality of outer shells comprise a foremost outer shell having a first end and a second end, the second end connected to the grasping members and a basement outer shell articulatedly connected to the first end of the foremost outer shell,
    wherein the plurality of power-transmission shafts are inserted in the basement outer shell and the foremost outer shell, and comprising a pair of claw power-transmission shafts operated independently from each other to actuate the pair of claw members of the grasping members, and
    wherein the claw members are configured to be operated independently from each other by respective independent operation of each of the claw power-transmission shafts around a first fulcrum pin defining a first fulcrum and fastened to the second end of the foremost outer shell in a first diametrical direction with respect to the second end of the foremost outer shell, and
    further comprising a first spring having a first end and a second end, the first end connected to a first one of the claw members and a second end connected to a second one of the claw members, the first spring extending around the first fulcrum to energize a tensile force to urge the claw members towards a closed position.

2. The multi-articulated manipulator defined in the claim 1, further comprising a first articulation joint operatively connecting the claw members of the grasping members to the second end of the foremost outer shell, and a second articulation joint articulatedly connecting the foremost outer shell to the basement outer shell.

3. The multi-articulated manipulator defined in the claim 1, wherein a base portion of the claw members comprises a cylindrical boss portion having the first fulcrum at the center thereof, and further comprising a spring connected between a first fixed pin held at an end of the spring to lie on a cylindrical surface of the boss portion and a second fixed pin held at another end of the spring and secured inside the foremost outer shell, the spring having a tensile force that pulls the claw members towards one another.

4. The multi-articulated manipulator defined in the claim 1, further comprising a second fulcrum pin fastened in a second diametrical direction with respect to respective joints between the foremost outer shell and the basement outer shell defining a second fulcrum, the foremost outer shell being connected via the second fulcrum pin to the basement outer shell so as to bend in a single direction around the second fulcrum.

5. The multi-articulated manipulator defined in the claim 4, further comprising a second spring mounted across the foremost outer shell and the basement outer shell to keep the foremost outer shell in a straight position with respect to the basement outer shell, wherein the second spring extends between a third pin fastened to the foremost outer shell and a fourth pin fastened to the basement outer shell, the second spring is disposed to extend through a location biased from the second fulcrum to thereby energize normally a spring force acting in a direction to pull mutually the foremost outer shell and the basement outer shell toward each other.

6. The multi-articulated manipulator defined in the claim 5, further comprising cut-away portions to relieve the second spring are defined in a lengthwise direction of respective ends of the foremost outer shell and the basement outer shell to extend in axial direction and facing towards the spring.

7. The multi-articulated manipulator defined in the claim 1, wherein each of the claw power-transmission shafts have a universal joint at a location corresponding to a joint between the foremost outer shell and the basement outer shell, and a first linkage mechanism to operate the claw members connected with the foremost outer shell around the first fulcrum in response to a bending movement between the foremost outer shell and the basement outer shell, and wherein the first linkage mechanism includes a first nut having first male threads mating with first female threads defined on a foremost end of the claw power-transmission shaft, and a first linkage member to connect the first nut with a respective one of the claw members, wherein during rotation of the claw power-transmission shaft, the first nut moves in an axial direction along the first male threads and the first linkage moves in the axial direction along the first male threads, whereby the first linkage member actuates the claw members around the first fulcrum.

8. The multi-articulated manipulator defined in the claim 7, further comprising lengthwise slits defined in the foremost end of the foremost outer shell to receive the first linkage members to protect the first linkage members against interference during rotation.

9. The multi-articulated manipulator defined in the claim 1, wherein the plurality of power-transmission shafts further comprises an outer shell power-transmitting shaft, the manipulator further comprising a second linkage mechanism to actuate the outer shell power-transmitting shaft the foremost outer shell relative to the basement outer shell, the second linkage mechanism being inserted into the basement outer shell to bend the foremost outer shell, wherein the second linkage mechanism is composed of a second male threads formed at the foremost end of the outer shell power-transmission shaft, a second nut having a second female threads mating with the second male threads, and a second linkage member to connect the second nut with the foremost outer shell, and wherein the second nut moves in an axial direction along the second male threads upon rotation of the outer shell power-transmitting shaft and the foremost outer shell moves so as to bend in the single direction around the second fulcrum point relatively to the basement outer shell.

\* \* \* \* \*